United States Patent
Klein et al.

(10) Patent No.: US 10,285,968 B2
(45) Date of Patent: May 14, 2019

(54) DRUG ELUTING EXPANDABLE DEVICES

(71) Applicant: CELONOVA BIOSCIENCES, INC., San Antonio, TX (US)

(72) Inventors: Richard Klein, Santa Rosa, CA (US); John Birtles, Sonoma, CA (US); John Koos, Penngrove, CA (US); Michael J. Lee, Santa Rosa, CA (US)

(73) Assignee: CELONOVA BIOSCIENCES, INC., San Antonio, TX (US)

( * ) Notice: Subject to any disclaimer, the term of this patent is extended or adjusted under 35 U.S.C. 154(b) by 0 days.

(21) Appl. No.: 15/920,316

(22) Filed: Mar. 13, 2018

(65) Prior Publication Data

US 2018/0200222 A1 Jul. 19, 2018

Related U.S. Application Data

(62) Division of application No. 14/801,944, filed on Jul. 17, 2015, now Pat. No. 9,949,944, which is a division of application No. 12/101,903, filed on Apr. 11, 2008, now Pat. No. 9,114,125.

(51) Int. Cl.
| | |
|---|---|
| A61K 31/337 | (2006.01) |
| A61L 29/14 | (2006.01) |
| A61F 2/82 | (2013.01) |
| A61L 31/18 | (2006.01) |
| A61L 31/08 | (2006.01) |
| A61L 29/10 | (2006.01) |
| A61K 31/44 | (2006.01) |
| A61L 31/16 | (2006.01) |
| A61L 31/14 | (2006.01) |
| A61L 29/18 | (2006.01) |
| A61L 29/16 | (2006.01) |

(52) U.S. Cl.
CPC .............. *A61K 31/337* (2013.01); *A61F 2/82* (2013.01); *A61K 31/44* (2013.01); *A61L 29/10* (2013.01); *A61L 29/146* (2013.01); *A61L 29/16* (2013.01); *A61L 29/18* (2013.01); *A61L 31/082* (2013.01); *A61L 31/146* (2013.01); *A61L 31/16* (2013.01); *A61L 31/18* (2013.01); *A61F 2230/0069* (2013.01); *A61F 2250/0067* (2013.01); *A61L 2300/00* (2013.01); *A61L 2300/204* (2013.01); *A61L 2300/21* (2013.01); *A61L 2300/602* (2013.01); *A61L 2300/606* (2013.01); *A61L 2300/608* (2013.01); *A61L 2300/802* (2013.01)

(58) Field of Classification Search
None
See application file for complete search history.

(56) References Cited

U.S. PATENT DOCUMENTS

| | | | |
|---|---|---|---|
| 4,944,745 A | 7/1990 | Sogard et al. | |
| 5,057,296 A | 10/1991 | Beck | |
| 5,102,643 A | 4/1992 | Kresge | |
| 5,516,781 A | 5/1996 | Morris et al. | |
| 5,622,684 A | 4/1997 | Pinnavaia et al. | |
| 5,807,306 A * | 9/1998 | Shapland ............ | A61M 25/104 604/21 |
| 5,882,329 A * | 3/1999 | Patterson ............ | A61B 17/3207 604/500 |
| 6,054,111 A | 4/2000 | Antonietti et al. | |
| 6,193,685 B1 | 2/2001 | Goodin | |
| 6,318,124 B1 | 11/2001 | Rutherford et al. | |
| 6,319,251 B1 * | 11/2001 | Tu ..................... | A61B 18/1492 606/194 |
| 6,334,988 B1 | 1/2002 | Gallis et al. | |
| 6,365,266 B1 | 4/2002 | MacDougall et al. | |
| 6,395,299 B1 | 5/2002 | Babich et al. | |
| 6,458,310 B1 | 10/2002 | Liu | |
| 6,465,365 B1 | 10/2002 | Annapragada | |
| 6,468,298 B1 | 10/2002 | Pelton | |
| 6,511,658 B2 | 1/2003 | Mattai et al. | |
| 6,541,539 B1 | 4/2003 | Yang et al. | |
| 6,592,764 B1 | 7/2003 | Stucky et al. | |
| 6,592,980 B1 | 7/2003 | MacDougall et al. | |
| 6,592,991 B1 | 7/2003 | Weisner et al. | |
| 6,730,064 B2 | 5/2004 | Ragheb et al. | |
| 6,991,802 B1 | 1/2006 | Ahola et al. | |
| 2002/0164380 A1 | 11/2002 | Ma et al. | |
| 2005/0080340 A1 | 4/2005 | Stewart et al. | |
| 2005/0119678 A1 | 6/2005 | O'Brien et al. | |

(Continued)

FOREIGN PATENT DOCUMENTS

| | | |
|---|---|---|
| EP | 0872447 A1 | 10/1998 |
| WO | 98/34723 A2 | 8/1998 |

(Continued)

OTHER PUBLICATIONS

Beck JS, et al., "A new family of mesoporous molecular sieves prepared with liquid crystal templates." J. Am. Chem. Soc., 1992, 114:10834-10843.

Brinker CJ, et al., "Evaporation-induced self-assembly: nanostrucutres made easy." Advanced Materials, 1999, 11 (7): 579-585.

Kresge CT, et al., "Ordered mesoporous molecular sieves synthesized by a liquid crystal template mechanism.", Nature, Oct. 1992, 359:710-712.

(Continued)

*Primary Examiner* — Robert A Wax
*Assistant Examiner* — Danah Al-Awadi
(74) *Attorney, Agent, or Firm* — Mannava & Kang, P.C.; Carol L. Bunner

(57) ABSTRACT

The present disclosure relates to drug eluting devices, and their uses. The drug eluting devices can allow for perfusion during deployment. The coatings the may contain bioactive materials which elute once deployed in a patient and can have anti-proliferative, anti-inflammation, or anti-thrombotic effects. Sol gel technology can be used to coat the devices.

10 Claims, 9 Drawing Sheets

(56) References Cited

U.S. PATENT DOCUMENTS

| | | | |
|---|---|---|---|
| 2006/0015170 A1* | 1/2006 | Jones | A61F 2/95 623/1.12 |
| 2006/0020243 A1 | 1/2006 | Speck et al. | |
| 2006/0051397 A1 | 3/2006 | Maier et al. | |
| 2006/0062820 A1 | 3/2006 | Gertner et al. | |
| 2006/0115512 A1 | 6/2006 | Peacock, III et al. | |
| 2006/0134160 A1* | 6/2006 | Troczynski | A61L 27/32 424/422 |
| 2006/0230476 A1 | 10/2006 | Atanasoska et al. | |
| 2007/0048348 A1* | 3/2007 | Atanasoska | A61L 29/08 424/423 |
| 2007/0071789 A1* | 3/2007 | Pantelidis | A61L 27/306 424/423 |
| 2007/0129748 A1* | 6/2007 | Eidenschink | A61F 2/958 606/192 |
| 2007/0207186 A1* | 9/2007 | Scanlon | A61F 2/07 424/424 |
| 2007/0244501 A1 | 10/2007 | Horn et al. | |
| 2007/0264303 A1 | 11/2007 | Atanasoska et al. | |
| 2008/0065200 A1 | 3/2008 | Binyamin et al. | |
| 2008/0146489 A1 | 6/2008 | Pacetti et al. | |
| 2008/0183278 A1 | 7/2008 | Atanasoska et al. | |
| 2008/0234810 A1 | 9/2008 | Carlson et al. | |
| 2010/0076542 A1 | 3/2010 | Orlowski | |

FOREIGN PATENT DOCUMENTS

| | | |
|---|---|---|
| WO | 99/36357 A1 | 7/1999 |
| WO | 99/47570 A1 | 9/1999 |
| WO | 00/66190 A1 | 4/2000 |
| WO | 00/25841 A1 | 5/2000 |
| WO | 00/29501 A1 | 5/2000 |
| WO | 2001/15751 | 3/2001 |
| WO | 01/28529 A1 | 4/2001 |
| WO | 02/058775 A2 | 8/2002 |
| WO | 03/055534 A1 | 7/2003 |
| WO | 2005/000740 A2 | 1/2005 |
| WO | 2005/082277 | 9/2005 |

OTHER PUBLICATIONS

Vallet-Regi M, et al., "A new property of MCM-41: drug delivery system." Chem. Mater., 2001, 13:308-311.

Munoz B, et al., "MCM-41 organic modification as drug delivery rate regulator." Chem. Mater., 2003, 15:500-503.

Schmidt-Winkel P, et al., "Microemulsion templating of siliceous mesostructured cellular foams with well-defined ultralarge mesopores." Chem. Mater., 2000, 12:686-696.

Khushalani D, et al., "Metamorphic materials: restructuring siliceous mesoporous materials." Advanced Materials, 1995, 7:842-846.

Galarneau A, et al., "Microporosity and connections between pores in SBA-15 mesostructured silicas as a function of the temperature of synthesis." New J. Chem., 2003, 27:73-79.

Xia Y, et al., "Soft lithography." Angew. Chem. Intl. Ed., 1998,37:550-575.

Trau M, et al., "Miroscopic patterning of orientated mesoscopic silica through guided growth." Nature, 1997, 390:674-676.

Holland BT, et al., "Synthesis of macroporous minerals with highly ordered three-dimensional arrays of spheroidal voids." Science, 1998, 281: 538-580.

Imhof A, et al., "Ordered macroporous materials by emulsion templating." Nature, 1997,389:948-951.

Yang P, et al., "Hierarchically ordered oxides." Science, 1998,282:2244-6.

Schuth, In: Studies in Surface Science and Catalysis, Galarneau A, et al (eds.), Proceedings of the Internaltional 13th Zeolite Conference, Montpellier, France, 2001, 135:1-12.

Doadrio AL, et al., "Mesoporous SBA-15 HPLC evaluation for controlled genamicin drug delivery." Journal of Controlled Release, 2004, 97(1):125-132.

Mal NK, et al., "Photocontrolled reversible release of guest molecules from coumarin-modified mesoporous silica." Nature, Jan. 2003, 242:350-353.

Axel DI, et al., "Paclitaxel inhibits arterial smooth muscle proliferation and migration in vitro and in vivo using local drug delivery." Circulation, 1997,96:636-645.

Drachman DE, et al., "Neointimal thickening after stent delivery of paclitaxel: change in composition and arrest of growth over six months." J. Am. Coil. Cardiol., 2000, 36:2325-2332.

Grube E, et al., "High-dose 7-hexanoyltaxol-eluting stent with polymer sleeves for coronary revascularization: one-year results from the SCORE randomized trial." J. Am. Coil. Cardiol., 2004, 44:1368-72.

Kortesuo P, "Sol-gel-processed sintered silica xerogel as a carrier in controlled drug delivery." Journal of Biomedical Materials Research, 1999,44:162-7.

Heldman AW, et al., "Paclitaxel stent coating inhibits neointimal hyperplasia at 4 weeks in a porcine model of coronary restenosis." Circulation, 2001, 103:2289-2295.

Dauskardt RH, et al., "Adhesion and debonding of multi-layer thin film structures." Engineering Fracture Mechanics, 1998, 61:141-162.

Kortesuo, P. "Sol-gel derived silica gel monoliths and microparticles as carrier in controlled drug delivery in tissue administration." Academic Dissertation, Dec. 2001.

* cited by examiner

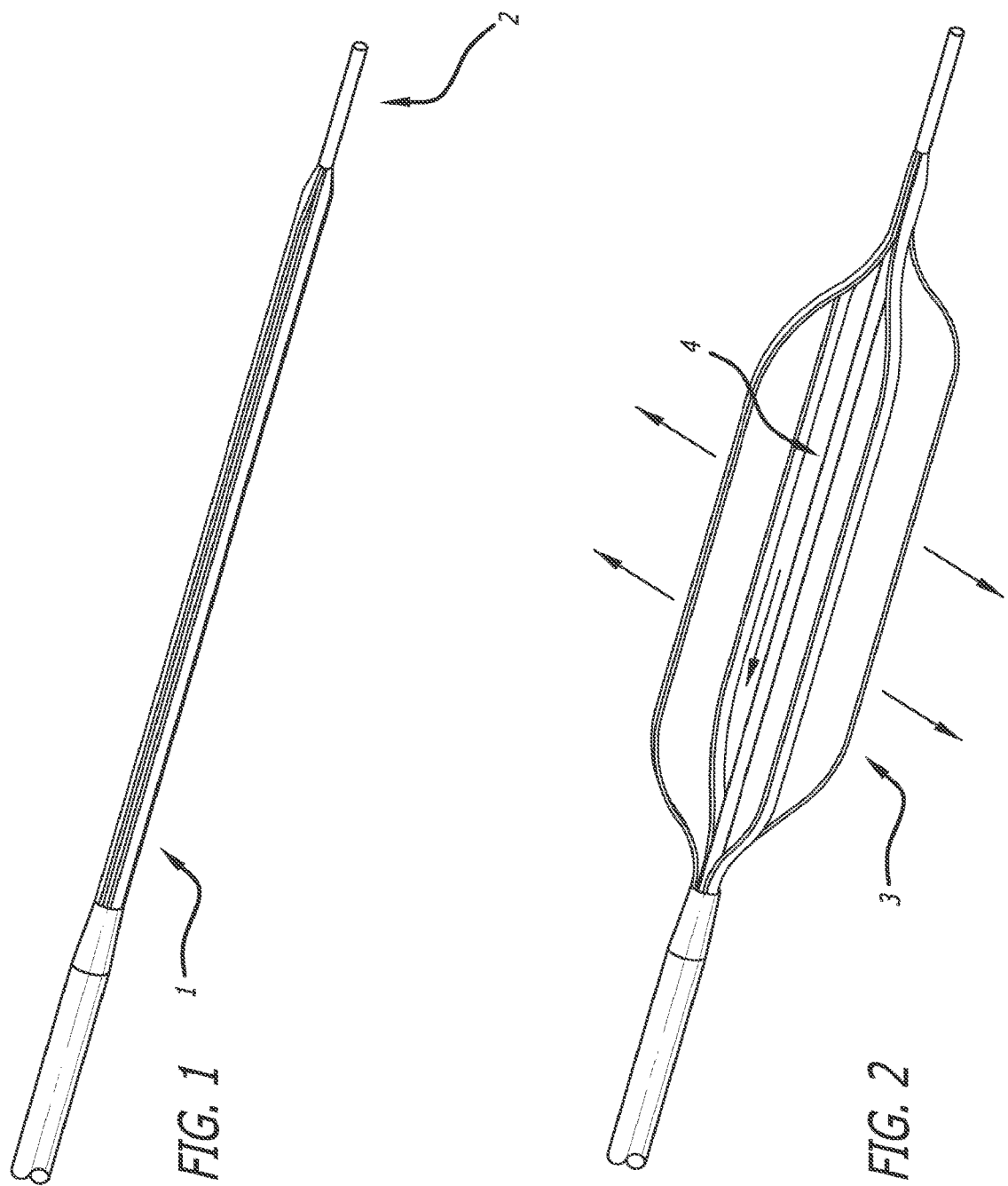

DRUG ELUTING EXPANDABLE DEVICES

RELATED APPLICATIONS

The present application claims priority to U.S. application Ser. No. 14/801,944, filed on Jul. 17, 2015, now allowed, which claims priority to U.S. Pat. No. 9,114,125, filed on Apr. 11, 2008, the disclosures of both of which are hereby incorporated by reference in their entirety.

FIELD OF THE INVENTION

The present disclosure relates to drug eluting expandable devices useful for medical treatments.

BACKGROUND OF THE INVENTION

"Sol-gel" processes are generally used to fabricate porous materials including self-assembled films. A sol is a liquid solution containing a colloid suspension of a material of interest dissolved in an appropriate solvent. Condensation reactions between the dissolved precursor molecules result in structures (particles, branched chains, linear chains, etc.) forming within the sol. The size, growth rate and morphology of these structures depend on the kinetics of the reactions within the solvent, which in turn are determined by parameters such as solution concentration, amount of water present, the temperature and pH of the solvent, agitation of the solvent and other parameters. Given enough time, condensation reactions will lead to the aggregation of growing particles or chains until eventually, a gel is formed. The gel can be visualized as a very large number of cross-linked precursor molecules forming a continuous, macroscopic-scale, solid phase, which encloses a continuous liquid phase consisting of the remaining solution. In the final steps of the sol-gel process, the enclosed solvent is removed (generally by drying) and the precursor molecules cross-link (a process called aging) resulting in the desired solid.

Sol-gel synthesis of materials offers several advantages over other synthetic routes. These advantages can include mild processing conditions (low temperature, low pressure, mild pH), inexpensive raw materials, no need for vacuum processing or other expensive equipment, and a high level of control over the resulting structure, particularly as it pertains to porosity. Regarding shape of the final product, there is essentially no limitation, because the liquid sol can be cast in any conceivable form before allowed to gel, including monoliths, thin films, fibers and micro- or nano-scale particles.

Porosity of materials produced in sol-gel processes can be controlled in a number of different ways. In the simplest sol-gel process, no special porogen is added to the sol and the porosity of the final solid is determined by the amount of precursor branching or aggregation before gelling. Average pore size, volume and surface area of porous sol-gel compositions increase with the size of the precursor molecules prior to the sol-gel processing.

Porosity can also be manipulated by the presence of additional materials within the solvent during the sol-gel process. The incorporation of sacrificial porogens in the sol (particularly those that can be easily removed via heating or other methods), is generally viewed as an efficient method to obtain porous solids when using sol-gel processes. Historically, these efforts were focused upon the fabrication of low dielectric constant (low-k) insulating films for the microelectronics industry. Sacrificial templates can also be used to create pores in inorganic materials formed using sol-gel processes. Sacrificial templates are usually amphiphilic molecules (i.e. those having hydrophilic and hydrophobic properties) capable of self-assembling in solution. These amphiphilic molecules create a highly-ordered structure that guides the precursor molecules to co-assemble around the structure. Once the precursor molecules co-assemble around the structure, it can be removed, leaving a negative image void.

Porous materials made using sol-gel processes can be used to deliver bioactive materials. For example, Vallet-Regi et al. (Chem. Mater. 2001, 13, 308-311) described charging powdered MCM-41 with ibuprofen. In this case, the ibuprofen was loaded into MCM-41 by dissolving the ibuprofen in hexane and adding the MCM-41 compound to the hexane in a powdered form. Munoz et al. (Chem. Mater. 2003, 15 500-503) described an experiment which demonstrated that ibuprofen could be delivered at a different rate from two different formulations of MCM-41, one made using a 16 carbon surfactant and one made using a 12 carbon surfactant.

Prior to International Patent Application Number PCT/US2004/040270 (PCT '270), which is fully incorporated by reference herein, no reference described an deployable medical device or bioactive material delivery device comprising a triblock copolymer template-based sol-gel composition formed surface coating with substantially continuously interconnected channels designed to function as a bioactive material reservoir. Moreover, no reference described a triblock copolymer template-based sol-gel composition surface coating with bioactive material found within the coating itself before being applied to the surface of a deployable medical device as well as having substantially continuously interconnected channels that could further function as a bioactive material reservoir after being applied to the surface of a deployable medical device. Thus, the invention described in PCT '270 provided at least two additional mechanisms through which bioactive materials could be loaded onto the surface of a deployable medical device.

While the materials and methods described in PCT '270 provided a number of important benefits (described therein), there is still room for improvement in the creation of bioactive material carrying materials made with sol-gel processes. For instance, better control of bioactive material particles during sol-gel processing and after device deployment could provide a benefit in allowing more accurate control over the amount of bioactive materials within a particular sol-gel composition as well as more control over the release rate of bioactive materials from a deployed medical device into the physiological environment after device deployment. The present disclosure provides such benefits. Before describing these benefits in more detail, however, background relating to a further aspect of the present invention is described.

The contents of US 2007/0071789 are herein incorporated by reference in its entirety. US 2007/0071789 describes implantable medical devices employing sol-gel composition coatings that function as a bioactive material reservoir, and the use of sol-gel composition coatings for improved adhesion of organic and inorganic substrates. The contents of U.S. application Ser. No. 10/528,577 also are herein incorporated by reference in its entirety. Ser. No. 10/528,577 describes medical devices that release drugs for the selective therapy of specific diseased tissues or organ parts, characterized in that lipophilic, largely water-insoluble drugs that bind to any tissue components adhere to the surfaces of devices that come into contact with the diseased tissue by being pressed against it at least for a short time and immediately release the active agent when in contact with tissue.

WO 2007/092043 describes implantable medical devices employing sol-gel composition coatings that functions as a bioactive material reservoir, and the use of sol-gel composition coatings for improved adhesion of organic and inorganic substrates. U.S. Pat. No. 6,764,690 discloses controllably dissolvable silica-xerogels prepared via a sol-gel process and a delivery device including controllably dissolvable silica-xerogel into which structure a bioactive material is incorporated. U.S. Pat. No. 6,544,223 discloses a device for delivering therapeutic agents and methods of making such a device. The device disclosed includes an inflatable balloon having holes in the walls of the balloon. U.S. Pat. No. 7,115,299 discloses inflatable porous balloons secured at a distal end of a catheter-based device with a composition including a polymer applied to the outer surface of the balloon.

U.S. Pat. No. 6,524,274 relates to a method for delivering a drug to tissue within the body by providing a catheter constructed for insertion in the body which carries a hydrogel. U.S. Pat. No. 7,066,904 relates to a catheter constructed for insertion in the body with a catheter shaft having an expandable hydrogel-coated porous balloon portion mounted on the catheter shaft. One of the disadvantages associated with U.S. Pat. Nos. 6,524,274 and 7,066,904 is that a separate or custom pH solution has to be mixed for inflation of the balloon. This would be too cumbersome. There also would be different inflation media versus the body pH or saline.

One challenge in the field of deployable medical devices has been adhering bioactive materials and bioactive material-containing coatings to the surfaces of deployable devices so that the bioactive materials will be released over time once the device is deployed. One approach to adhering bioactive materials to substrates, such as the surface of deployable medical devices has been to include the bioactive materials in polymeric coatings. Polymeric coatings can hold bioactive materials onto the surface of deployable medical devices, and release the bioactive materials via degradation of the polymer or diffusion into liquid or tissue (in which case the polymer is non-degradable). While polymeric coatings can be used to adhere bioactive materials to deployed medical devices, there are problems associated with their use. One problem is that adherence of a polymeric coating to a substantially different substrate, such as a stent's metallic substrate, is difficult due to differing characteristics of the materials (such as differing thermal expansion properties). Further, most inorganic solids are covered with a hydrophilic native surface oxide that is characterized by the presence of surface hydroxyl groups (M-OH, where M represents an atom of the inorganic material, such as silicon or aluminum). At ambient conditions then, at least a monolayer of adsorbed water molecules covers the surface, forming hydrogen bonds with these hydroxyl groups. Therefore, due to this water layer, hydrophobic organic polymers cannot spontaneously adhere to the surface of the deployable medical device. Furthermore, even if polymer/surface bonds (including covalent bonds) are formed under dry conditions, those bonds are susceptible to hydrolysis (i.e. breakage) upon exposure to water. This effect is particularly important in applications where devices or components containing organic/inorganic interfaces must operate in aqueous, corrosive environments such as a human or other animal's body. These difficulties associated with adhering two different material types often leads to inadequate bonding between the deployable medical device and the overlying polymeric coating which can result in the separation of the materials over time. Such separation is an exceptionally undesirable property in a deployed medical device.

Two different approaches have traditionally been followed to reinforce organic/inorganic interfaces. The first is the introduction of controlled roughness or porosity on an inorganic surface that induces polymer mechanical interlocking. The second is chemical modification of the inorganic surface via amphiphilic silane coupling agents that improve polymer wetting, bonding and interface resistance to water. While these methods provide some benefits, they are not effective in all circumstances. Thus, there is room for improvement in methods associated with adhering inorganic and organic surfaces. Certain sol-gel composition embodiments according to the present invention provide such improvements.

Paclitaxel coated catheters can have long inflation times. They can also have contra-indicated ischemic plots, proximal lesions/left main coronary artery and a high degree of washout which can be greater than 80%. Weeping catheters/balloons can also have long inflation times with a high degree of washout which can be greater than 95%. Dual balloons can also have long inflation times and be traumatic to a healthy vessel. There is a need for a drug eluting medical device which has an expandable member coated with sol gel technology, which overcomes the shortcomings of prior art devices.

US 2006/0020243 describes a paclitaxel coated catheter which has disadvantages. One is that it has long inflation times. Clinical trials required one minute inflation time. This long inflation time limits the population which can be treated and can lead to ischemic events. Embodiments according to the present disclosure utilize perfusion whereas US 2006/0020243 does not. Perfusion provides the improvement which would reduce ischemic event. Also, the devices according to US 2006/0020243 have a high degree of drug washout due to poor coating. The present disclosure relates to devices which overcome the disadvantages of prior art devices and methods such as disclosed in US 2006/0020243.

SUMMARY OF THE INVENTION

The present disclosure relates to drug eluting expandable devices which avoids many of the drawbacks of prior art drug eluting devices. Certain embodiments of the presently disclosed devices allow for perfusion which can reduce ischemic events during deployment. Also, the present devices feature robust adhesion of the bioactive material to expandable members such as balloons. Also, the instant sol gel drug eluting devices allow for adjustable release rate of the bioactive materials. Another advantage is the minimization of washout. This is especially important when the bioactive materials to be eluted are cytotoxic substances such as paclitaxel. The presently disclosed sol gel drug eluting devices also can have thin sol gel coatings with minimal effect on profile, rewrap, thickness and flexibility.

The present disclosure generally relates to drug eluting expandable devices, methods of making such devices and their uses. Specifically, the present disclosure provides for drug eluting medical devices having an expandable member which may be used for treating intravascular or endolumenal diseases or other abnormal conditions. Sol gel technology can be used to coat the expandable member. The coatings may contain bioactive materials which may elute once deployed in a patient and can have anti-proliferative, anti-inflammation, or anti-thrombotic effects.

One embodiment of the present disclosure relates to a drug eluting device comprising an expandable member and at least one coating on the expandable member comprising at least one layer, wherein the at least one layer of the at least one coating comprises an adjustable matrix composition comprising a sol gel material and a bioactive material. In another embodiment, the expandable member is a balloon or a basket. In another embodiment, the balloon is a cutting balloon. In another embodiment the basket comprises a material including, but not limited to, shape memory metal, shape memory metal alloy, or a superelastic material. In one embodiment, the material is nickel titanium. The basket can be self-expanding or manually expanding. In an embodiment, the basket comprises a metal, polymer, ceramic, or other blends or combinations thereof. In another embodiment, the expandable member is in association with a fixed wire system.

In one embodiment, the bioactive material comprises at least one of an anti-restenotic agent, an anti-inflammatory agent, an HMG-CoA reductase inhibitor, an antimicrobial agent, an antineoplastic agent, an angiogenic agent, an anti-angiogenic agent, a thrombolytic agent, an antihypertensive agent, an anti-arrhythmic agent, a calcium channel blocker, a cholesterol-lowering agent, a psychoactive agent, an anti-depressive agent, an anti-seizure agent, a contraceptive, an analgesic, a bone growth factor, a bone remodeling factor, a neurotransmitter, a nucleic acid, an opiate antagonist; a statin including, but not limited to cervistatin; paclitaxel; and combinations thereof.

In one embodiment, the coating comprises two or more layers, each layer comprising an adjustable matrix composition and a bioactive material. The at least one layer may comprise a sol gel material. In another embodiment, the two or more layers are different from each other.

In another embodiment, the sol-gel material comprises at least one of an organic oxide, inorganic oxide, an organically modified silane, and a hybrid oxide comprising an organically modified silane and an organic oxide or inorganic oxide. The inorganic oxides may comprise at least one of an oxide of silicon, an oxide of titanium, and an oxide of aluminum. In one embodiment, the organically modified silane has the formula $(R^2)_3—SiR^1$, wherein $R^1$ is independently selected from substituted alkyl, substituted alkenyl, substituted alkynyl, substituted aralkyl, substituted heteroaryl, and substituted alkoxy with the proviso that $R^1$ contains a hydroxyl or amino group, or a functional group that can be transformed to a radical that contains a hydroxyl or amino group; wherein $R^2$ is independently selected from halo, optionally substituted alkoxy, optionally substituted aryloxy, optionally substituted silyloxy, or optionally substituted alkyl with the proviso that all three $R^2$ substituents are not simultaneously substituted alkyl.

In another embodiment, the organically modified silane is selected from the group consisting of Tetraethoxysilane, Tetramethoxysilane, Methyltriethoxysilane, Methyltrimethoxysilane, ethyltriethoxysilane, ethyltrimethoxysilane, Tetrapropylorthosilicate, Phenyltriethoxysilane, Phenyltrimethoxysilane, Isobutyltriethoxysilane, Isobutyltrimethoxysilane, Diphenyldiethoxysilane, Diphenyldimethoxysilane, Dimethyl(diethoxy)silane, Dimethyl (dimethoxy)silane, Propyltrimethoxysilane, Propyltriethoxysilane, 3-aminopropyltriethoxysilane (AES), 3-aminopropyltrimethoxysilane, (3-Glycidoxypropyl) trimethoxysilane, (3-Glycidoxypropyl) triethoxysilane, Hydroxymethyltriethoxysilane, Hydroxymethyltrimethoxysilane, 3-(hydroxyl(polyethyleneoxy)propyl)-heptamethyltrisiloxane, N-(2'-aminoacyl)-3-aminopropyltriethoxysilane, 3-Gluconamidopropylsiloxane, 3-methacryloxypropyltrimethoxysilane, 3-methacryloxypropyltriethoxysilane, Vinyltrimethoxysilane, Vinyltriethoxysilane, N-β-aminoethyl-γ-aminopropyltrimethoxysilane, N-β-aminoethyl-γ-aminopropylmethyldimethoxysilane, N-methyl-γ-aminopropylmethyldiethoxysilane, Acetoxypropyltrimethoxysilane, Hydridotrimethylsilane, Hydridotriethylsilane, Chloromethyltrimethoxysilane, Chloromethyltriethoxysilane, Cyclohexyltrimethoxysilane, 3-(2-aminoethylamino)propyltrimethoxysilane (EDAS), 3-(2-aminoethylamino) propyltriethoxysilane (EDAES), Fluoroalkylsilanes, Diethoxymethylvinylsilane, Diethoxymethylphenylsilane, [(N,N-diethylamino)propyl] trimethoxysilane, Anilinomethyltriethoxysilane, and Anilinomethyltrimethoxysilane.

In another embodiment, the adjustable matrix composition comprises an inorganic oxide and an agent that modifies a characteristic of the inorganic oxide selected from the group consisting of hydrophobicity, charge, biocompatibility, mechanical properties, bioactive material affinity, storage capacity, and combinations thereof.

In another embodiment, the expandable member comprises a porous or non-porous material. In another embodiment, the expandable member comprises a polymer including, but not limited to, polyamide, polyolefin, polyethylene, polyester, polyurethane, elastomer, thermoplastic elastormer, nylon elastomer, nylon, nylon blends, copolyamide block ether, polyether block amides (PEBAX), polyethylene terephthalate (PET), polytetrafluoroethylene (PTFE), expanded polytetrafluoroethylene (ePTFE), latex, or silicone; or blends or combinations thereof.

In another embodiment, the adjustable matrix composition is adjusted to provide a specific release rate of said bioactive material.

In another embodiment, the coating is non-uniform. The coating can cover only a portion of the device including, but not limited to, the abluminal portion, just the luminal portion, the proximal portion, the distal portion, and/or the central portion. In another embodiment the coating is deposited in a gradient over the length of the device. In another embodiment, the coating is in the form of dots or stripes or other non-contiguous pattern.

Another embodiment of the present disclosure relates to a medical system comprising a stent and a drug eluting device comprising an expandable member and at least one coating on said expandable member comprising at least one layer, wherein said at least one layer of said at least one coating comprises an adjustable matrix composition comprising a sol gel material and a bioactive material. In one embodiment, the stent is a bare metal stent or a drug eluting stent. In another embodiment, the system further comprises a delivery catheter. In one embodiment, the drug eluting stent contains the same bioactive material as that of the drug eluting device. In another embodiment, the drug eluting stent contains a different bioactive material from that of the drug eluting device.

Another embodiment of the present disclosure relates to a drug eluting device comprising a balloon and at least one coating on the balloon comprising at least one layer, wherein the at least one layer of the at least one coating comprises a bioactive material, wherein the device allows for perfusion during deployment. In one embodiment, the coating further comprises a contrast media. In another embodiment, the coating further comprises a sol gel material. In another embodiment, the coating is non-uniform. In another embodiment, the coating is in the form of dots or stripes or other non-contiguous pattern.

In another embodiment, the drug eluting device further comprises a multilumen tubular member comprising two or more lumens, the multilumen tubular member comprising a proximal end and a distal end extending through a balloon cavity defined by the balloon. In one embodiment, the multilumen tubular member is a bilumen tubular member comprising at least one side opening arranged in the bilumen tubular member located both distal and proximal of the balloon and in fluid communication with one another via a first lumen in the bilumen tubular member, the first lumen extending from the proximal end of the bilumen tubular member through the tubular member to an end hole distal of the balloon; and the second lumen is provided for receiving a pressure fluid for inflating the balloon.

In another embodiment, the drug eluting device further comprises an axially elongate catheter shaft, constructed and arranged for insertion into a distal body lumen, said catheter shaft having an inflation conduit extending axially therethrough; the balloon secured to said catheter shaft, the balloon in fluid communication with the inflation conduit and outwardly radially expandable to a preselected configuration in response to inflation thereof. In one embodiment, the balloon is multi-lobed.

In another embodiment, the drug eluting device further comprises an inflatable member having generally a helically coiled portion, the helically coiled portion being inflatable from a deflated configuration to an inflated, configuration defining a generally open lumen.

Another embodiment of the present disclosure relates to a method of treating stenosis or restenosis or in-stent restenosis comprising deploying in a subject a drug eluting device comprising an expandable member and least one coating on the expandable member comprising at least one layer, wherein the at least one layer of the at least one coating comprises an adjustable matrix composition comprising a sol gel material and a bioactive material. In another embodiment, the device allows for perfusion during deployment.

Another embodiment of the present disclosure relates to a method of treating stenosis or restenosis or in-stent restenosis comprising deploying in a subject a drug eluting device comprising an expandable member and at least one coating on the device comprising at least one layer, wherein the at least one layer of the at least one coating comprises a bioactive material and a contrast media, wherein the device allows for perfusion during deployment. In another embodiment, the expandable member is a balloon and the at least one coating is deposited on and adhered to the balloon.

BRIEF DESCRIPTION OF THE DRAWINGS

FIG. 1 depicts a drug eluting medical device having an expandable member in the compressed state which can be self or manually expanded.

FIG. 2 depicts a drug eluting medical device having expandable ribs in their expanded state.

DETAILED DESCRIPTION OF THE INVENTION

Figure 3:
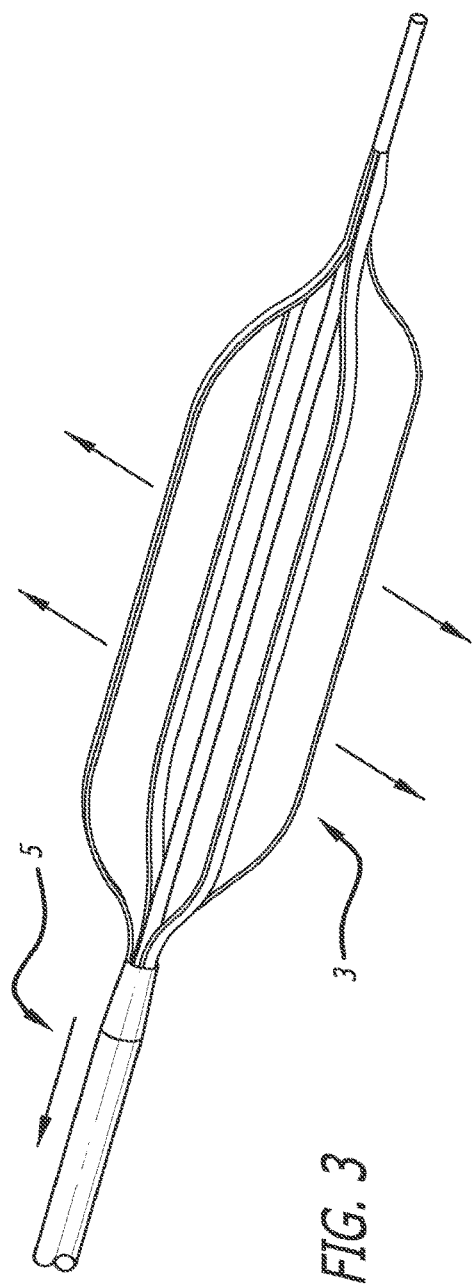
FIG. 3 depicts a drug eluting medical device having expandable ribs which are self-expanding.

One embodiment of the present disclosure relates to a drug eluting device comprising an expandable member and at least one coating on the expandable member comprising at least one layer, wherein the at least one layer of the at least one coating comprises an adjustable matrix composition comprising a sol gel material and a bioactive material.

As used herein adjustable matrix refers to an admixture that can be optimized to control retention time on an expandable member's surface as well as the bioactive agent dose delivered to a treatment site.

A sol gel material is defined herein broadly to cover the product of a sol-gel process. This typically involves preparation of a sol, gelation of the sol and removal of the solvent. The sol may be produced from inorganic or organic precursors (e.g. nitrates or alkoxides) and may consist of dense oxide particles or polymeric clusters. A sol is defined as a colloidal suspension of solid particles in a liquid. There can be particulate sols and polymeric sols: the difference can be defined in terms of size. Particulate sols contain dense oxide particle typically about 1 nm in size. Polymeric sols generally contain long, hairy, branched suspensions of particles. Any precursor consisting of a metal or metalloid element surrounded by a set of ligands, which includes alkoxides, can be used to prepare a colloidal system. This colloidal system can then be used to form a gel in accordance with the present disclosure. A gel herein is defined as a substance that contains a continuous solid skeleton enclosing a continuous liquid phase.

The sol gel process typically involves the manufacture of inorganic matrices or ceramics through the formation of a sol or suspension in solution. Hydrolysis and condensation of appropriate precursors (typically metal alkoxides or metal chlorides) leads to the formation of colloidal or polymeric gels which extend throughout the liquid (thereby entrapping the liquid). Hence, condensation drives the conversion process from sol to gel such that a continuous, globally connected solid polymeric matrix is produced and a wet gel is formed. Polycondensation within a silicon based sol is possible due to the hydrolytic susceptibility of Si—O—Si based polymers. The labile nature of this bond fuels the growth of polymeric networks which then form gels which can then in turn form a porous solid material when the liquid is removed and the material is subsequently dried. 'Aging' or perhaps additional high temperature drying can push the condensation process even further such that the material may shrink or its surface chemistry may change or its pore size distribution may shift.

In one embodiment, the sol gel material may comprise at least one of an organic oxide, an inorganic oxide, an organically modified silane, and a hybrid oxide comprising an organically modified silane and an inorganic oxide. In another embodiment, the inorganic oxide comprises at least one of an oxide of silicon, an oxide of titanium, and an oxide of aluminum.

The term "organically modified" refers to compounds that contain at least one organic (carbon-based) ligand (in one embodiment a direct metal-carbon (or semiconductor-carbon) bond). The term "organically modified silane" refers to a compound that contains at least one non-hydrolysable carbon-based ligand bonded to silicon. This class of compounds is also referred to as ORMOSILs, silane coupling agents, silane couplers, silane adhesion promoters, or simply silanes. These compounds represent a wide variety of compounds because the non-hydrolysable ligand(s) can be any conceivable organic group(s) synthesized according to the principles of organic chemistry. Non-limiting examples include alkylsilanes (such as, but not limited to, methyltrimethoxysilane, methyltriethoxysilane, dimethyldiethoxysilane, trimethylethoxysilane, vinyltrimethoxysilane, vinyltriethoxysilane, ethyltriethoxysilane, isopropyltriethoxysilane, butyltriethoxysilane, octyltriethoxysilane, dodecyltriethoxysilane, octadecyltriethoxysilane, etc), arylfunctional silanes (e.g. phenyltriethoxysilane, etc.), aminosilanes (e.g. aminopropyltriethoxysilane, aminophenyltrimethoxysilane, aminopropyltrimethoxysilane, etc.), acrylate- and methacrylate-functional silanes (e.g. acryloxypropyltrimethoxysilane, ect), carboxylate, phosphonate, ester, sulfonate, isocyanate, and epoxy functional silanes.

It is important to realize that these compounds still contain hydrolysable groups that enable them to undergo hydrolysis/condensation reactions of sol-gel processes. Therefore, each of them or any combination of two or more of them can be used as sol-gel precursors, or they can be used in combination with a fully hydrolysable sol-gel precursor, such as tetraethoxy silane (TEOS) or titanium isopropoxide. The sol-gel composition thus obtained will not be a stoichiometric inorganic oxide. Instead it will be a hybrid sol-gel material that will exhibit bulk chemical, mechanical, physical and other properties characteristic of the particular combination of constituent components.

Exemplary organically modified silanes that can be particularly useful in this aspect include silane having the formula $(R^2)_3$—$SiR^1$, wherein $R^1$ is independently selected from substituted alkyl, substituted alkenyl, substituted alkynyl, substituted aralkyl, substituted heteroaryl, and substituted alkoxy with the proviso that $R^1$ contains a hydroxyl or amino group, or a functional group that can be transformed to a radical that contains a hydroxyl or amino group; wherein $R^2$ is independently selected from halo, optionally substituted alkoxy, optionally substituted aryloxy, optionally substituted silyloxy, or optionally substituted alkyl with the proviso that all three $R^2$ substituents are not simultaneously substituted alkyl. Alternatively, exemplary organically modified silanes may include Tetraethoxysilane, Tetramethoxysilane, Methyltriethoxysilane, Methyltrimethoxysilane, ethyltriethoxysilane, ethyltrimethoxysilane, Tetrapropylorthosilicate, Phenyltriethoxysilane, Phenyltrimethoxysilane, Isobutyltriethoxysilane, Isobutyltrimethoxysilane, Diphenyldiethoxysilane, Diphenyldimethoxysilane, Dimethyl(diethoxy)silane, Dimethyl(dimethoxy)silane, Propyltrimethoxysilane, Propyltriethoxysilane, 3-aminopropyltriethoxysilane (AES), 3-aminopropyltrimethoxysilane, (3-Glycidoxypropyl) trimethoxysilane, (3-Glycidoxypropyl)triethoxysilane, Hydroxymethyltriethoxysilane, Hydroxymethyltrimethoxysilane, 3-(hydroxyl(polyethyleneoxy)propyl)-heptamethyltrisiloxane, N-(2'-aminoacyl)-3-aminopropyltriethoxysilane, 3-Gluconamidopropylsiloxane, 3-methacryloxypropyltrimethoxysilane, 3-methacryloxypropyltriethoxysilane, Vinyltrimethoxysilane, Vinyltriethoxysilane, N-β-aminoethyl-γ-aminopropyltnmethoxysilane, N-β-aminoethyl-γ-aminopropylmethyldimethoxysilane, N-methyl-γ-aminopropylmethyldiethoxysilane, Acetoxypropyltrimethoxysilane, Hydridotrimethylsilane, Hydridotriethylsilane, Chloromethyltrimethoxysilane, Chloromethyltriethoxysilane, Cyclohexyltrimethoxysilane, 3-(2-aminoethylamino)propyltrimethoxysilane (EDAS), 3-(2-aminoethylamino)propyltriethoxysilane (EDAES), Fluoroalkylsilanes, Diethoxymethylvinylsilane, Diethoxymethylphenylsilane, [(N,N-diethylamino)propyl] trimethoxysilane, Anilinomethyltriethoxysilane, and Anilinomethyltrimethoxysilane In another embodiment, the adjustable matrix composition can comprise an inorganic oxide and an agent that modifies a characteristic of the inorganic oxide selected from the group consisting of hydrophobicity, charge, biocompatibility, mechanical properties, bioactive material affinity, storage capacity; and combinations thereof. An organically modified silane can be such an agent. By varying the properties of the sol-gel composition, different bioactive material delivery release rates and profiles can be achieved for various bioactive materials. For example, a bioactive material can be released with first order or second order kinetics. Delivery can begin upon deployment of the bioactive material delivery device, or at a particular time after implantation, and can increase rapidly from zero to a maximal rate over a short period of time, for example less than an about 5 minutes. Such maximal delivery can continue for a predetermined period until the delivery rate suddenly drops. In the field of sustained-release bioactive material delivery it is generally considered desirable to avoid a large bioactive material delivery "burst" wherein the majority of the bioactive material is delivered in a short amount of time. However in some cases the delivery of a "burst" of bioactive material is highly desirable such as a PCTA or PTA drug coated balloon whose residence time in the treatment area is short lived. The methods of the present disclosure that allow for incorporation of bioactive material into the forming sol-gel composition can be used to tailor the release kinetics. Embodiments adopting treating the surface and/or channels of the sol-gel composition with an organically modified silane can also be used to either speed up or slow the rate of drug elution. In accordance with the present disclosure then, a variety of parameters can be adjusted to produce numerous variations in delivery profiles depending on what is desirable for a particular bioactive material/disease/patient combination.

The expandable member according to the present disclosure can be a balloon or a basket. The expandable member can be in association with a fixed wire system. The basket can be self-expanding or manually expanding. In another embodiment, the basket comprises a material that comprises a shape memory metal, shape memory metal alloy, or a superelastic material. In another embodiment, the material is nickel titanium. Superelastic materials possess superelasticity which is an impermanent response to relatively high stress caused by a phase transformation between the austenitic and martensitic phases. When mechanically loaded, a superelastic alloy deforms reversibly to very high strains by the creation of a stress-induced phase. When the load is removed, the new phase becomes unstable and the material regains its original shape. Alternatively, the basket comprises a metal, polymer, ceramic, or other blends or combinations thereof. The term "basket" can also refer to a cage.

In another embodiment, the balloon can be a cutting balloon. A cutting balloon has a special balloon tip with small blades which are activated when the balloon is inflated.

The term "bioactive material(s)" as used herein refers to any organic, inorganic, or living agent that is biologically active or relevant. For example, a bioactive material can be a protein, a polypeptide, a polysaccharide (e.g. heparin), an oligosaccharide, a mono- or disaccharide, an organic compound, an organometallic compound, or an inorganic compound. It can include a biologically active molecule such as a hormone, a growth factor, a growth factor-producing virus, a growth factor inhibitor, a growth factor receptor, an anti-inflammatory agent, an antimetabolite, an integrin blocker, or a complete or partial functional insense or antisense gene. It can also include a man-made particle or material, which carries a biologically relevant or active material. An example is a nanoparticle comprising a core with a drug and a coating on the core. Such nanoparticles can be post-loaded into pores or co-deposited with metal ions.

Bioactive materials also can include drugs such as chemical or biological compounds that can have a therapeutic effect on a biological organism. Bioactive materials include those that are especially useful for long-term therapy such as hormonal treatment. Examples include drugs for contraception and hormone replacement therapy, and for the treatment of diseases such as osteoporosis, cancer, epilepsy, Parkinson's disease and pain. Suitable biological materials can include, without limitation, an anti-restenotic agent, an anti-inflammatory agent, an HMG-CoA reductase inhibitor, an antimicrobial agent, an antineoplastic agent, an angiogenic agent, an anti-angiogenic agent, a thrombolytic agent, an antihypertensive agent, an anti-arrhythmic agent, a calcium channel blocker, a cholesterol-lowering agent, a psychoactive agent, an anti-depressive agent, an anti-seizure agent, a contraceptive, an analgesic, a bone growth factor, a bone remodeling factor, a neurotransmitter, a nucleic acid, an opiate antagonist and combinations thereof. Additional bioactive materials include, without limitation, paclitaxel, rampamycin, everolimus, tacrolimus, sirolimus, des-aspartate angiotensin I, nitric oxide, apocynin, gamma-tocopheryl, pleiotrophin, estradiol, aspirin, statin, atorvastatin, cerivastatin, fluvastatin, lovastatin, pravastatin, rosuvastatin, simvastatin, and combinations thereof.

Bioactive materials also can include precursor materials that exhibit the relevant biological activity after being metabolized, broken-down (e.g. cleaving molecular components), or otherwise processed and modified within the body. These can include such precursor materials that might otherwise be considered relatively biologically inert or otherwise not effective for a particular result related to the medical condition to be treated prior to such modification.

Combinations, blends, or other preparations of any of the foregoing examples can be made and still be considered bioactive materials within the intended meaning herein. Aspects of the present invention directed toward bioactive materials can include any or all of the foregoing examples.

There are various ways to apply a bioactive active material to the expandable members including balloons of the present drug eluting devices. These methods include spraying or dip coating. More specifically, application methods include electrospinning, sol spinning, or electrostatic spraying. Dip coating could include rotation of an expandable member such as a balloon. The balloon can be held above a solution containing a bioactive material and can be parallel to the surface. The balloon can be partially submerged such that it rotates a portion of the balloon to give it time to dry before it return to the solution on the next rotation. Dip coating can also include vertical dipping. The teachings of U.S. Pat. No. 6,764,690 are herein incorporated by reference in its entirety. U.S. Pat. No. 6,764,690 generally teaches spraying drying particles onto a surface. In addition, the bioactive materials may be applied by vapor phase deposition.

In another embodiment, the coating on the expandable member of the present drug eluting expandable devices may comprise two more layers, each layer comprising an adjustable matrix composition and a bioactive material. In another embodiment, the adjustable matrix is a sol gel material. In another embodiment, the two or more layers of the coating are different from each other.

Contrast media is any substance that is used to enhance the visibility of structures or fluids within the body. An example of this is the use of a radiopaque substance during an x-ray exam to highlight features that would otherwise be less distinguishable from nearby tissue. The contrast can either be positive or negative. Positive contrast media has a higher attenuation density than the surrounding tissue. This means that the contrast looks more opaque than the surrounding tissue when seen on an x-ray. Negative contrast media has a lower attenuation density than the surrounding tissue. This means that the contrast looks less opaque than the body. Negative contrast is generally found as a gas. Contrast can be used to produce images of almost any hollow structure in the body.

In another embodiment, the coating(s) or the layer(s) on the expandable member of the present drug eluting devices may be non-uniform. Without limitation, they may be contiguous or non-contiguous. Without limitation, they may be in the form of dots or stripes.

In another embodiment, the expandable member of the present drug eluting devices can comprise a porous or non-porous material. In another embodiment, the expandable member comprises a polymer. Alternatively, the polymer may comprise polyamide, polyolefin, polyethylene, polyester, polyurethane, elastomer, thermoplastic elastormer, nylon elastomer, nylon, nylon blends, copolyamide block ether, polyether block amides (PEBAX), polyethylene terephthalate (PET), polytetrafluoroethylene (PTFE), expanded polytetrafluoroethylene (ePTFE), latex, or silicone; or blends or combinations thereof.

Figure 4:
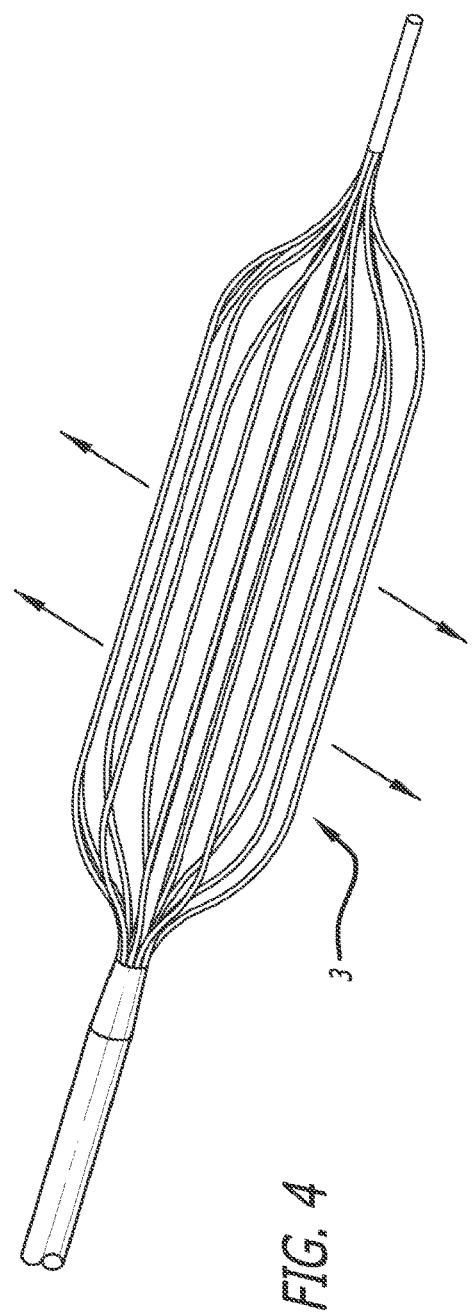
FIG. 4 depicts a drug eluting medical device with twelve expandable ribs in their expanded state.

FIG. 1 depicts a drug eluting medical device having an expandable member in the compressed state which can be self or manually expanded. The expandable ribs are in the compressed state 1. A flexible tip 2 is shown which can be associated with a guide wire or an over-the-wire type device. FIG. 2 depicts a drug eluting medical device having expandable ribs 3 which are shown in their expanded state. For a manual expansion design, the center component 4 can act as a pull wire to activate the expansion of the ribs. FIG. 3 depicts a drug eluting device having expandable ribs which are self expanding. When the ribs are self expanded, a sheath 5 could be retracted to allow the ribs 3 to expand. The ribs can be coated with bioactive materials. FIG. 3 shows four ribs for the expandable member. However, the number of ribs can be greater than four in various embodiments. FIG. 4 depicts a drug eluting medical device with twelve expandable ribs 3 in their expanded state. The ribs can be manually or self-expanded. The ribs can be coated with bioactive material. The ribs of FIGS. 1-4 can be a mesh, or weave, or can be filaments at various angles, unparallel to each other and can be of various shapes, widths, and thicknesses.

Figure 5:
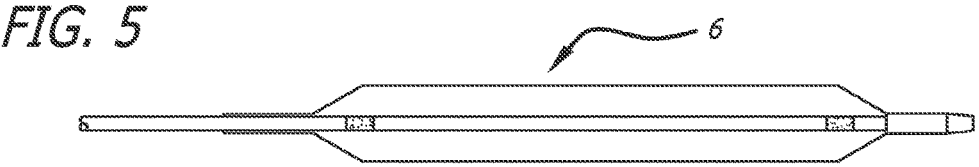
FIG. 5 depicts a drug eluting medical device with a balloon having a coating on its surface.
Figure 6:
FIG. 6 depicts another drug eluting medical device with a balloon having a coating on its working length.
Figure 7:
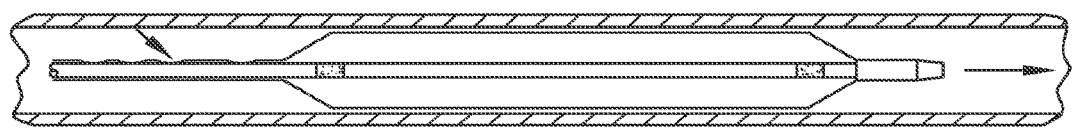
FIG. 7 depicts a drug eluting medical device having an expandable member which allows for perfusion.
Figure 8:
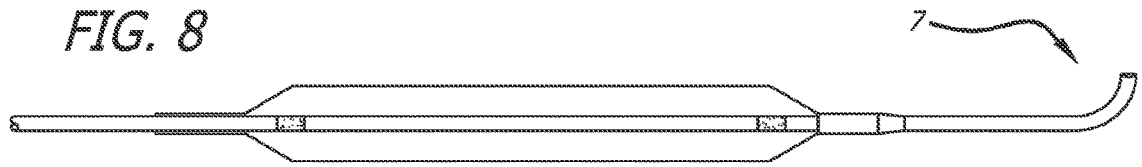
FIG. 8 depicts a drug eluting medical device having an expandable member in association with a fixed wire system.

FIG. 5 shows a drug eluting medical device with a balloon having a coating on its surface 6. FIG. 6 depicts another drug eluting medical device with a balloon having coating on its working length (shown by shading). In this embodiment, the coating is on the middle cylindrical portion which would be in contact with a vessel when expanded. FIG. 7 depicts a drug eluting medical device which allows for perfusion. The arrows show movement of blood during deployment. FIG. 8 depicts a drug eluting medical device having an expandable member in association with a fixed wire 7 system, wherein the wire component is integrated with the expandable member device.

Figure 9A:
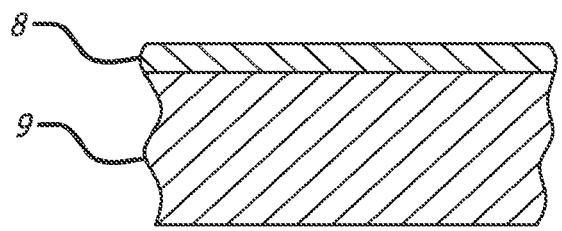
FIGS. 9A-9D depict substrates with coatings.
Figure 9B:
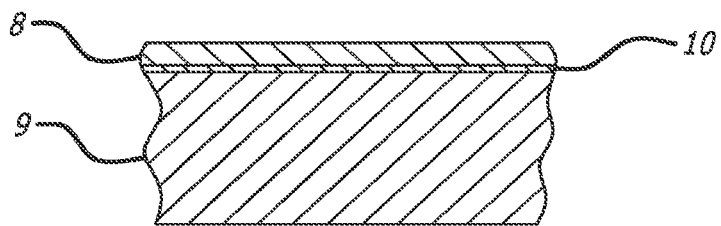
Figure 9C:
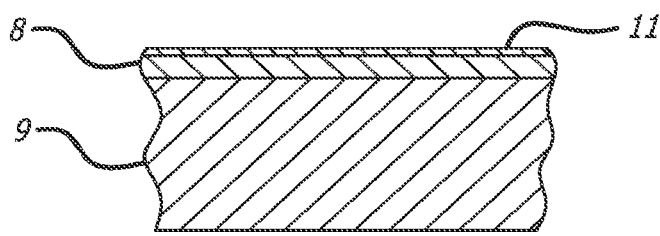
Figure 9D:
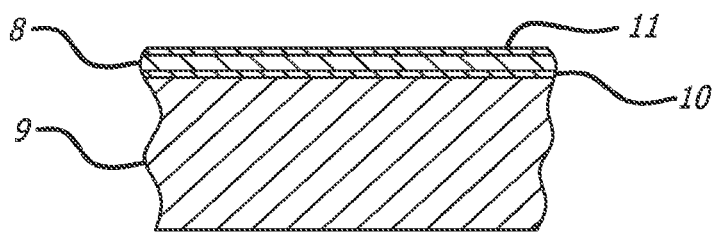

FIGS. 9A-9D depict substrates with coatings. In FIG. 9A the drug matrix 8 is shown which has been applied to a substrate 9. FIG. 9B shows an additional layer which is a tie layer 10. FIG. 9C shows yet another additional layer which is a top layer 11. FIG. 9D shows the tie layer 10, drug matrix 8, and a top layer 11 on a substrate 9.

Figure 10A:
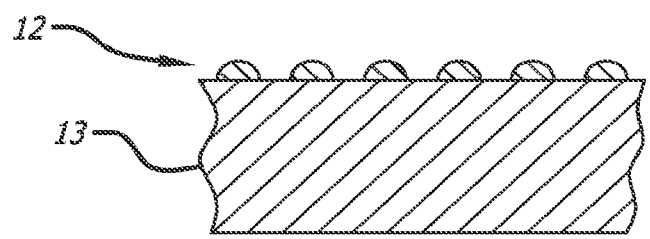
FIGS. 10A and 10B depict substrates with coatings having non-uniform layers.
Figure 10B:
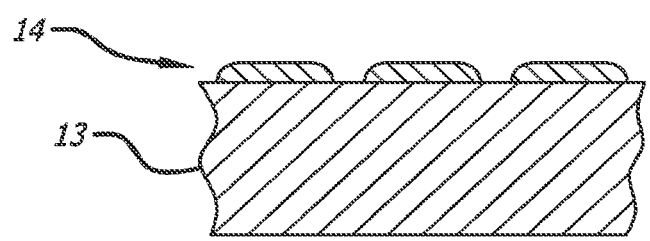

FIGS. 10A and 10B depict substrates with coatings and layers which are irregular or non-uniform. 12 and 14 are drug matrix on the substrate 13.

Perfusion as used herein permits blood flow through the drug eluting expandable device from the proximal to the distal end during deployment. This reduces the risk of ischemic events. When the expandable member is a basket, there would be natural perfusion through the openings in the basket. When the expandable member is a balloon which can cause complete occlusion when deployed, openings may be necessary to allow blood flow.

Another embodiment of the present disclosure relates to a medical system comprising a stent and a drug eluting device comprising an expandable member and at least one coating on the expandable member comprising at least one layer, wherein the at least one layer of the at least one coating comprises an adjustable matrix composition comprising a sol gel material and a bioactive material. Alternatively, the stent can be a bare metal stent or a drug eluting stent. A stent generally is a tube that is inserted into a natural conduit of the body to prevent or counteract a disease-induced localized flow constriction. A bare metal stent is made of metal and generally does not elute drug. A drug-eluting stent is a stent placed typically into narrowed, diseased arteries that slowly releases a drug to block cell proliferation. This prevents scar-tissue-like growth that, together with clots (thrombus), could otherwise block the stented artery, a process called restenosis. In another embodiment, the medical system allows for perfusion during deployment. In another embodiment the medical system further comprises a delivery catheter. A catheter is a tube that can be inserted into a body cavity, duct or vessel. Catheters thereby allow drainage or injection of fluids or access by surgical instruments. A delivery catheter allows for delivery of medical equipment. A delivery catheter herein can be used to deliver the present medical system comprising a stent and a drug eluting device. Or it can be used to delivery only a drug eluting device. In another embodiment, the drug eluting stent contains the same bioactive material as that of the drug eluting device. Or the drug eluting stent can contain a different bioactive material from that of the drug eluting device.

Another embodiment of the present disclosure relates to a drug eluting device comprising a balloon and at least one coating on the balloon comprising at least one layer, wherein the at least one layer of the at least one coating comprises a bioactive material, wherein the device allows for perfusion during deployment. In another embodiment, the coating can further comprise of contrast media. In another embodiment, the coating further comprises a sol gel material. In another embodiment, the coating is non-uniform. Alternatively, the coating can be in the form of dots or stripes.

In another embodiment, the drug eluting device further comprises a multilumen tubular member comprising two or more lumens, the multilumen tubular member comprising a proximal end and a distal end extending through a balloon cavity defined by the balloon. In one embodiment, the multilumen tubular member is a bulilumen tubular member comprising at least one side opening arranged in the bilumen tubular member located both distal and proximal of the balloon and in fluid communication with one another via a first lumen in the bilumen tubular member, the first lumen extending from the proximal end of the bilumen tubular member through the tubular member to an end hole distal of the balloon; and the second lumen is provided for receiving a pressure fluid for inflating the balloon. One of ordinary skill in the art is directed to the teachings of U.S. Pat. No. 5,295,961 contents of which are herein incorporated by reference in its entirety. U.S. Pat. No. 5,295,961 offers a general teaching of a catheter system for mechanical dilatation of coronary stenoses.

In another embodiment, the drug eluting device further comprises an axially elongate catheter shaft, constructed and arranged for insertion into a distal body lumen, said catheter shaft having an inflation conduit extending axially therethrough; the balloon secured to said catheter shaft, the balloon in fluid communication with the inflation conduit and outwardly radially expandable to a preselected configuration in response to inflation thereof. In one embodiment, the balloon is multi-lobed. One of ordinary skill in the art is directed to the teachings of U.S. Pat. No. 4,983,167 contents of which are herein incorporated by reference in its entirety. U.S. Pat. No. 4,983,167 offers a general teaching of a catheter system which provides a path for conducting blood past a stenosis and inflated balloons (perfusion). In another embodiment, the balloon is multi-lobed.

In another embodiment, the drug eluting device further comprises an inflatable member having generally a helically coiled portion, the helically coiled portion being inflatable from a deflated configuration to an inflated, configuration defining a generally open lumen. One of ordinary skill in the art is directed to the teachings of U.S. Pat. No. 5,181,911 contents of which are herein incorporated by reference in its entirety. U.S. Pat. No. 5,181,911 offers a general teaching of a helical balloon catheter which allows for perfusion.

Another embodiment of the present disclosure relates to a method of treating stenosis or restenosis or in-stent restenosis comprising deploying in a subject a drug eluting device comprising an expandable member and at least one coating on the expandable member comprising at least one layer, wherein the at least one layer of the at least one coating comprises an adjustable matrix composition comprising a sol gel material and a bioactive material. In another embodiment, the device allows for perfusion during deployment.

Another embodiment of the present disclosure relates to a method of treating stenosis or restenosis or in-stent restenosis comprising deploying in a subject a drug eluting device comprising an expandable member balloon and at least one coating on the device comprising at least one layer, wherein the at least one layer of the at least one coating comprises a bioactive material and a contrast media, wherein the device allows for perfusion during deployment. In another embodiment, the expandable member is a balloon and the at least one coating is deposited on and adhered to the balloon.

EXAMPLES

Example 1: Coating of an Expanded Balloon with a Paclitaxel Containing Sol-Gel Matrix A solution containing 0.2M of TEOS in a mixture of water and ethanol was hydrolyzed for 3 hours at pH 3. Paclitaxel was then added to the silane based solution such that the final concentration of drug was 5 mg/ml. This solution was then sprayed at a flow rate of 40 μl/min via an ultrasonic nozzle (operating at 120 KHz) onto a balloon (3.25 mm×19 mm) which in turn was moving at a predefined lateral speed (10 mm/second) and rotation rate (3 Hz) through the spray plume.

The balloon was coated by moving the balloon back and forth through the ultrasonically generated spray plume a total of 5 times (referred to as 'passes'). A 'rest period' of 90-120 seconds was included between successive passes in order to allow the matrix to dry and in turn promote additional cross-linking within the sol-gel.

At this time the balloon was allowed to dry for 16-24 hours before evaluating the elution characteristics of the encapsulated drug. The balloon was placed in different 1 ml aliquots of PBS (Phosphate Buffered Saline) for a series of defined times in order to generate the appropriate elution profile.

Figure 14:
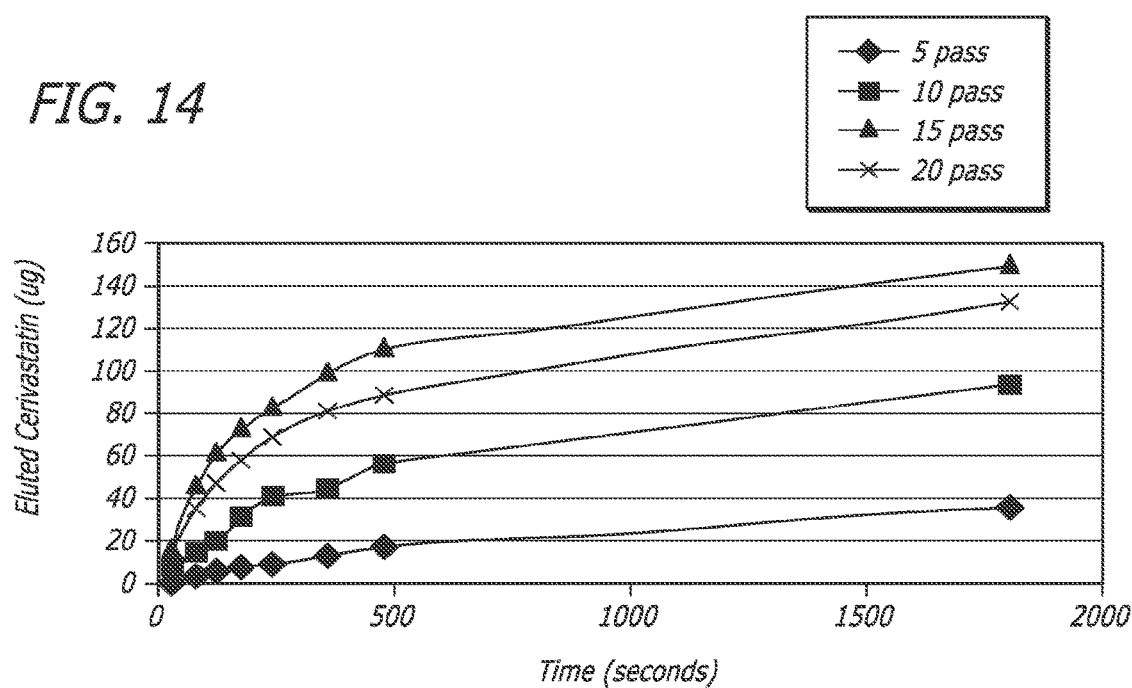
FIG. 14 is a drug elution curve for an expanded balloon with a paclitaxel containing sol-gel matrix.

The aliquots of PBS were then analyzed by HPLC to establish paclitaxel concentrations in solution at each time point. The data is presented in FIG. 14.

Figure 11A:
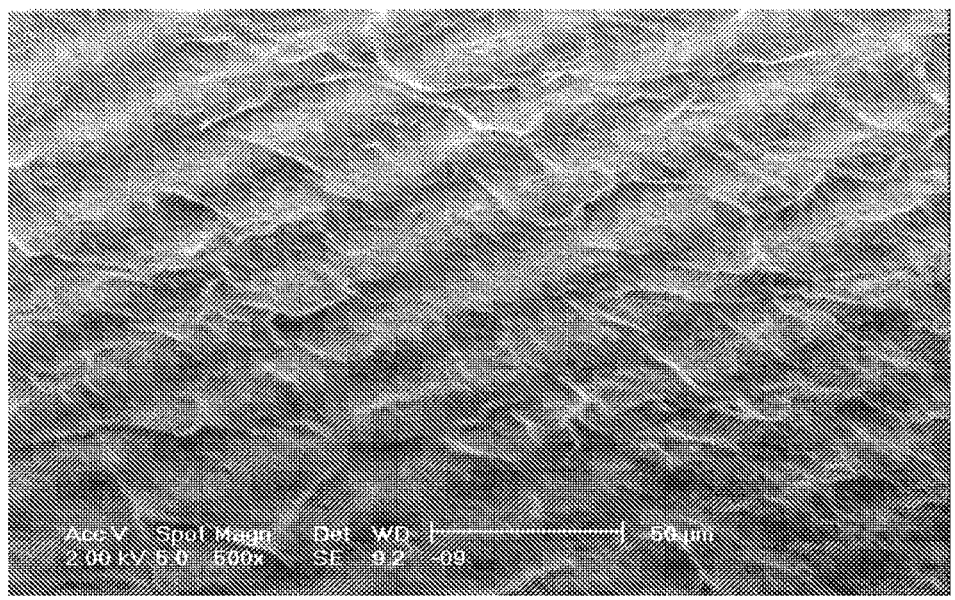
FIGS. 11A and 11B show scanning electron microscope (SEM) images of paclitaxel sol-gel sprayed balloon.
Figure 11B:
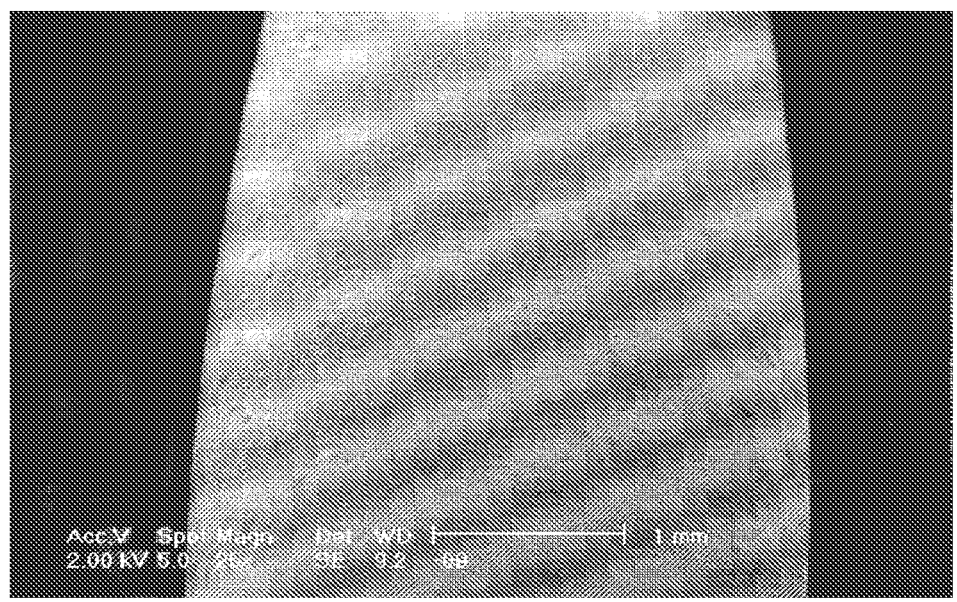

A series of optical photographs and SEM images were also collected prior to performing the elution analysis in order to evaluate coating adhesion and integrity of the coating. A FEI XL-30 SEM was used to acquire the images shown in FIGS. 11A and 11B. The following parameters were used to acquire the SEM images: accelerating voltage=2 kV, Current=2 mA, working distance=10 mm to 30 mm.

Example 2: Coating of an Expanded Balloon with a Cerivastatin-Containing Sol-Gel Matrix A solution containing 20% isobutyltriethoxysilane and 80% TEOS (for a combined total concentration of 0.2M) in a mixture of water and ethanol was hydrolyzed for 3 hours at pH 3. Cerivastatin was then added to the silane based solution such that the final concentration of drug was 5 mg/ml. This solution was then sprayed at a flow rate of 40 μl/min via an ultrasonic nozzle (operating at 120 KHz) onto a balloon (3.25 mm×19 mm) which in turn was moving at a predefined lateral speed (10 mm/second) and rotation rate (3 Hz) through the spray plume.

The balloon was coated by moving the balloon back and forth through the ultrasonically generated spray plume a total of 5 times. A 'rest period' of 90-120 seconds was included between successive passes in order to allow the matrix to dry and in turn promote additional cross-linking within the sol-gel. This procedure was repeated with different balloons (10 and 20 times respectively) to include variable numbers of passes and hence therefore variable quantities of drug within the matrix (and hence on the balloon).

At this point the balloon was allowed to dry for 16-24 hours before evaluating the elution characteristics of the encapsulated drug. The balloon was placed in different 1 ml aliquots of PBS for a series of times in order to generate the appropriate elution profile.

Figure 15:
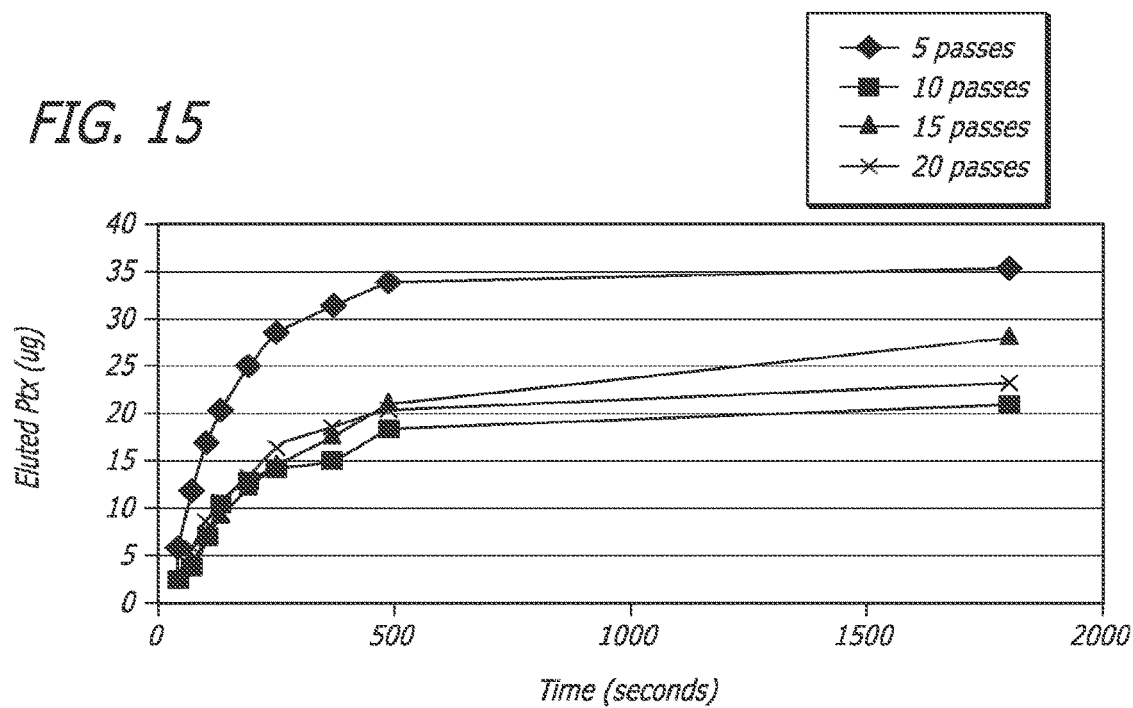
FIG. 15 is a drug elution curve for an expanded balloon with a cerivastatin containing sol-gel matrix.

The aliquots of PBS were then analyzed by HPLC to establish cerivastatin concentrations in solution at each time point. The data is presented below in FIG. 15.

Figure 12:
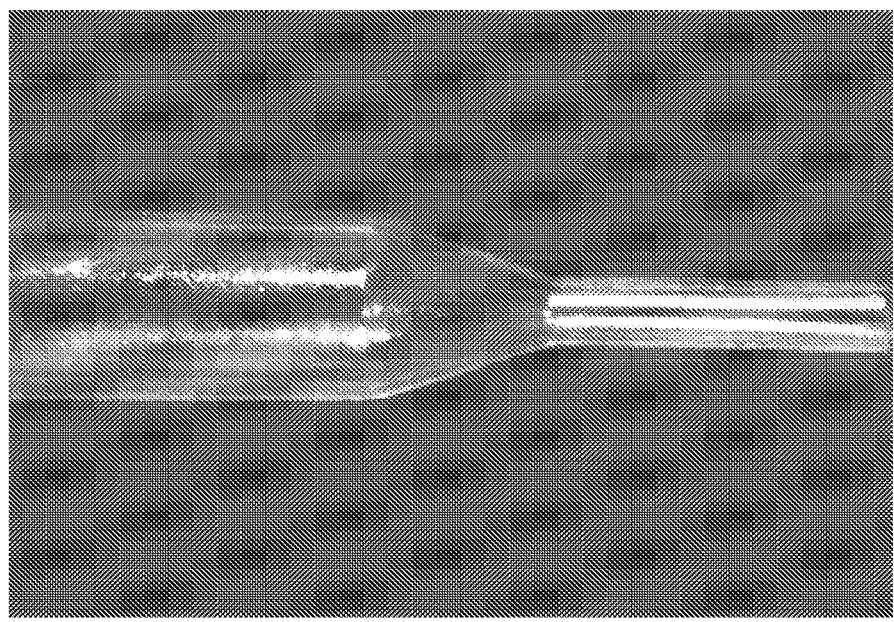
FIG. 12 is an optical image of an expanded balloon with a cerivastatin containing sol-gel matrix.
Figure 13:
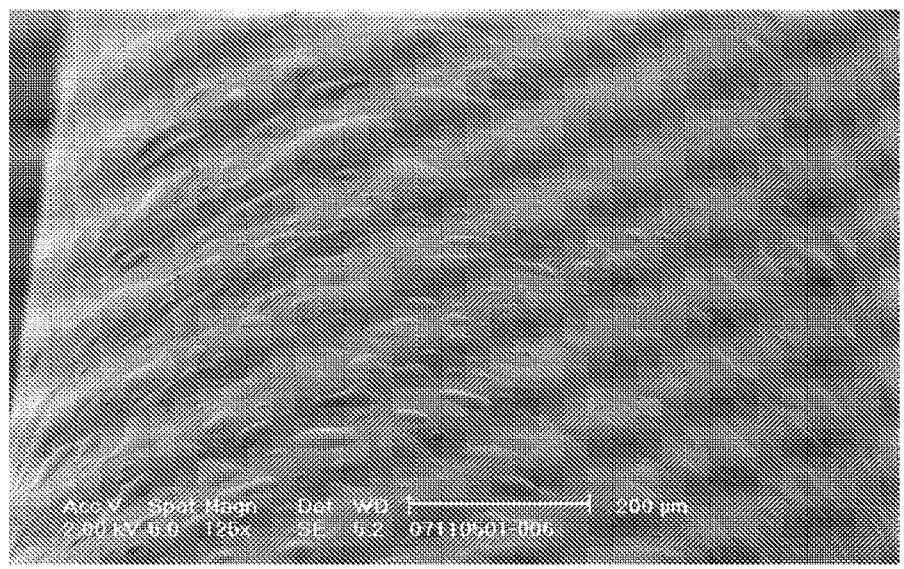
FIG. 13 is a scanning electron microscope (SEM) image of an expanded balloon with a cerivastatin containing sol-gel matrix.

A series of optical photographs and SEM images were also collected prior to performing the elution analysis in order to evaluate coating adhesion and integrity of the coating. A FEI XL-30 SEM was used to acquire the images shown in FIGS. 12 and 13. The following parameters were used to acquire these images: accelerating voltage=2 kV, Current=2 mA, working distance=10 mm to 30 mm.

Example 3: Coating of an Expanded Balloon with a Paclitaxel Containing Sol-Gel Matrix A solution containing 10% isobutyltriethoxysilane and 90% TEOS (for a combined total concentration of 0.2M) in a mixture of water and ethanol was hydrolyzed for 3 hours at pH 3. Paclitaxel was then added to the silane based solution such that the final concentration of drug was 12 mg/ml. This solution was then sprayed at a flow rate of 40 μl/min via an ultrasonic nozzle (operating at 120 KHz) onto a balloon (3.25 mm×19 mm) which in turn was moving at a predefined lateral speed (10 mm/second) and rotation rate (3 Hz) through the spray plume.

The balloon was coated by moving the balloon back and forth through the ultrasonically generated spray plume a total of 5 times. A 'rest period' of 90-120 seconds was included between successive passes in order to allow the matrix to dry and in turn promote additional cross-linking within the sol-gel. This procedure was repeated with another balloon a total of 10 times such that twice as much drug was placed on the balloon within the sol-gel based matrix.

At this time the balloon was allowed to dry for 16-24 hours before evaluating the elution characteristics of the encapsulated drug. The balloon was placed in different 1 ml aliquots of PBS for a series of defined times in order to generate the appropriate elution profile.

Figure 16:
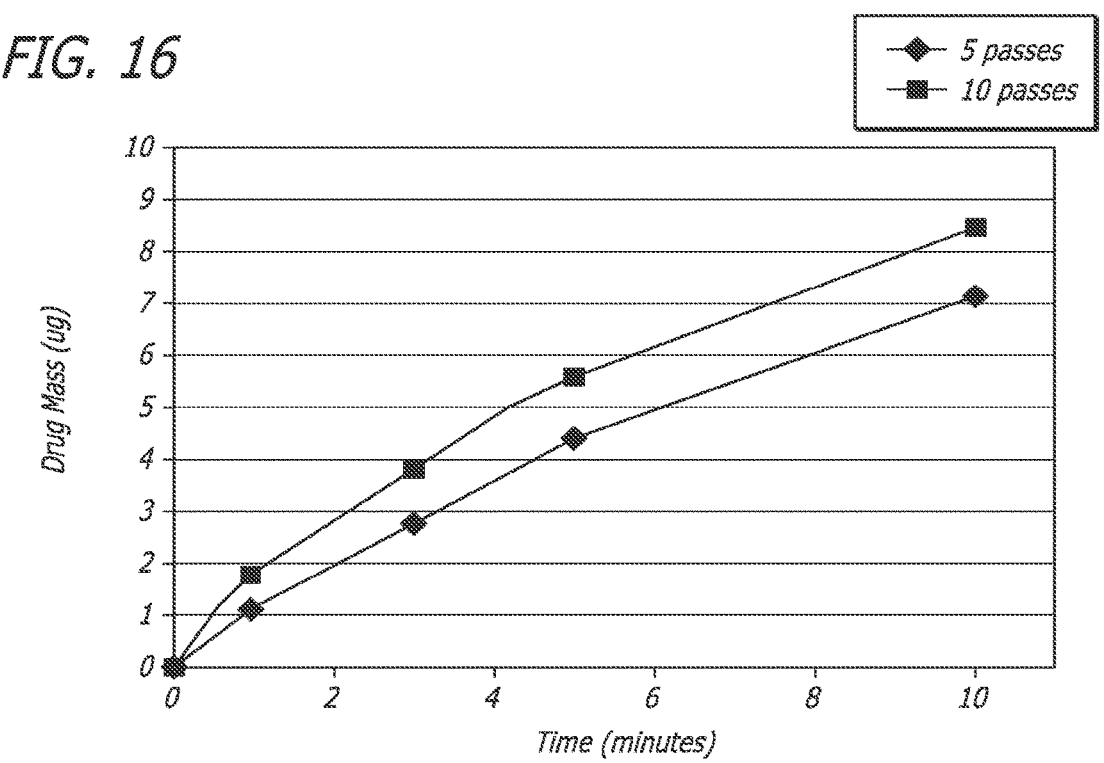
FIG. 16 is another drug elution curve for an expanded balloon with a paclitaxel containing sol-gel matrix.

The aliquots of PBS were then analyzed by HPLC to establish paclitaxel concentrations in solution at each time point. The data is presented below in FIG. 16.

Example 4: Coating of an Expanded Balloon with a Cerivastatin Containing Sol-Gel Matrix A solution containing 20% isobutyltriethoxysilane and 80% TEOS (for a combined total concentration of 0.2M) in a mixture of water and ethanol was hydrolyzed for 3 hours at pH 3. Cerivastatin was then added to the silane based solution such that the final concentration of drug was either 8.5 mg/ml or 12.4 mg/ml. These solutions were then sprayed at a flow rate of 40 μl/min via an ultrasonic nozzle (operating at 120 KHz) onto a balloon (3.25 mm×19 mm) which in turn was moving at a predefined lateral speed (10 mm/second) and rotation rate (3 Hz) through the spray plume. In using this approach, the quantity of drug contained within a set amount of matrix material was varied. This, in turn, allows the user to vary the amount of drug that elutes from the matrix within a set time.

The balloon was coated by moving the balloon back and forth through the ultrasonically generated spray plume a total of 5 times. A 'rest period' of 90-120 seconds was included between successive passes in order to allow the matrix to dry and in turn promote additional cross-linking within the sol-gel.

At this point the balloon was allowed to dry for 16-24 hours before evaluating the elution characteristics of the encapsulated drug. The balloon was placed in different 1 ml aliquots of PBS for a series of times in order to generate the appropriate elution profile.

Figure 17:
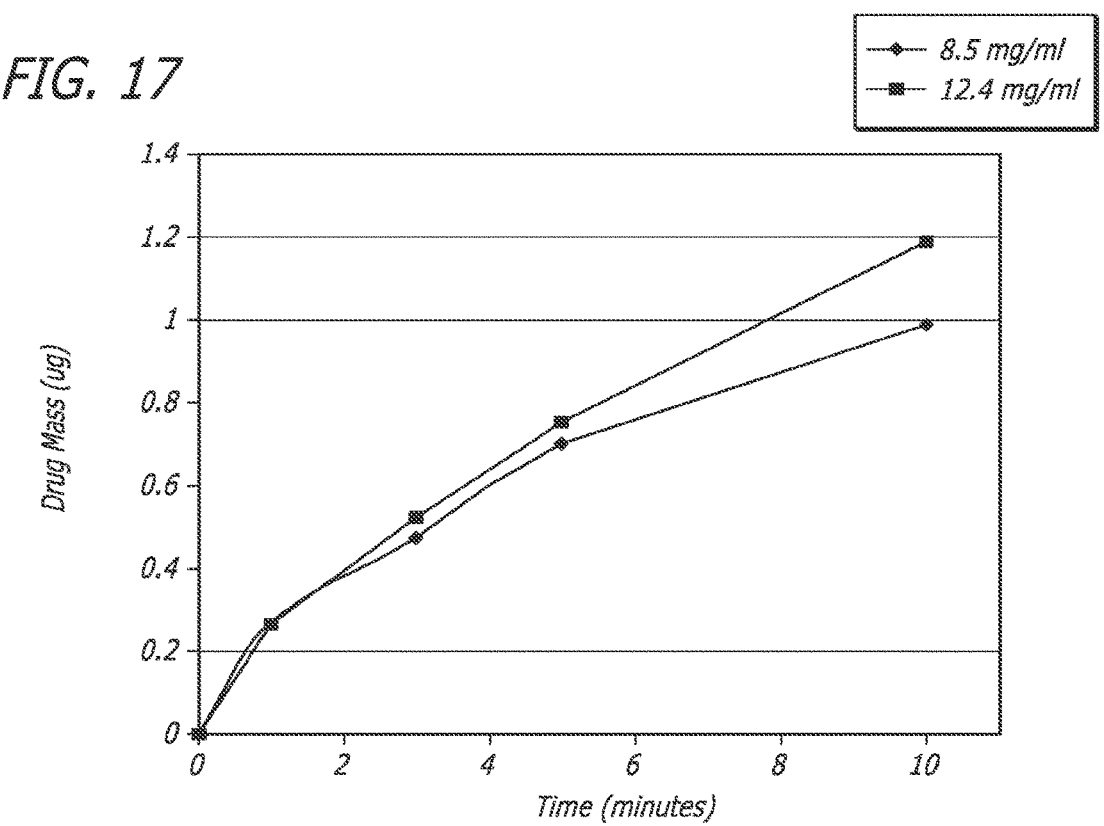
FIG. 17 is another drug elution curve for an expanded balloon with a cerivastatin containing sol-gel matrix.

The aliquots of PBS were then analyzed by HPLC to establish cerivastatin concentrations in solution at each time point, for each variable set of passes. The data is presented below in FIG. 17.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A drug eluting device comprising an expandable member and at least one coating on said expandable member comprising at least one layer, wherein said at least one layer of said at least one coating comprises an adjustable matrix composition comprising a sol gel material and a bioactive material, wherein the expandable member is a basket including a center component that acts as a pull wire to activate expansion of the expandable member and a flexible tip associated with a guide wire.

2. The drug eluting device of claim 1, wherein said basket comprises a material that comprises a shape memory metal, shape memory metal alloy, or a superelastic material.

3. The drug eluting device of claim 2, wherein the material is nickel titanium.

4. The drug eluting device of claim 1, wherein the basket is manually expanding.

5. The drug eluting device of claim 1, wherein the basket comprises a metal, polymer, ceramic or other blends or combinations thereof.

6. The drug eluting device of claim 1, wherein the bioactive material comprises at least one of an anti-restenotic agent, an anti-inflammatory agent, an HMG-CoA reductase inhibitor, an antimicrobial agent, an antineoplastic agent, an angiogenic agent, an anti-angiogenic agent, a thrombolytic agent, an antihypertensive agent, an anti-arrhythmic agent, a calcium channel blocker, a cholesterol-lowering agent, a psychoactive agent, an anti-depressive agent, an anti-seizure agent, a contraceptive, an analgesic, a bone growth factor, a bone remodeling factor, a neurotransmitter, a nucleic acid, an opiate antagonist; and combinations thereof.

7. The drug eluting device of claim 1, wherein said coating comprises two or more layers, each layer comprising an adjustable matrix composition and a bioactive material.

8. The drug eluting device of claim 7, wherein at least one layer comprises a sol gel material.

9. The drug eluting device of claim 7, wherein said two or more layers are different from each other.

10. The drug eluting device of claim 7, wherein the coating further comprises a contrast media.

\* \* \* \* \*